United States Patent
Boyd et al.

(10) Patent No.: US 6,934,357 B2
(45) Date of Patent: Aug. 23, 2005

(54) METHODS AND APPARATUS FOR MOTION COMPENSATION IN IMAGE RECONSTRUCTION

(75) Inventors: Douglas Perry Boyd, Hillsborough, CA (US); Geordie Henry Zapalac, Nevada City, CA (US); Peter Michael Edic, Albany, NY (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 83 days.

(21) Appl. No.: 10/625,719

(22) Filed: Jul. 23, 2003

(65) Prior Publication Data

US 2004/0136501 A1 Jul. 15, 2004

Related U.S. Application Data

(60) Provisional application No. 60/398,463, filed on Jul. 25, 2002, and provisional application No. 60/397,658, filed on Jul. 23, 2002.

(51) Int. Cl.$^7$ ............................................ G01N 20/083
(52) U.S. Cl. .............................. 378/62; 378/8; 378/901
(58) Field of Search ........................... 378/4, 8, 20, 62, 378/901

(56) References Cited

U.S. PATENT DOCUMENTS

| | | | |
|---|---|---|---|
| 5,491,734 A | 2/1996 | Boyd et al. | |
| 5,719,914 A | 2/1998 | Rand et al. | |
| 5,933,006 A | * 8/1999 | Rasche et al. | ............... 324/307 |
| 6,130,929 A | 10/2000 | Saha | |
| 6,208,711 B1 | 3/2001 | Rand et al. | |

* cited by examiner

*Primary Examiner*—David V Bruce
(74) *Attorney, Agent, or Firm*—Carl B. Horton Esq.; Armstrong Teasdale LLP

(57) ABSTRACT

A method for facilitating a reduction in motion artifacts includes comparing two sequential scanned images to determine motion.

35 Claims, 3 Drawing Sheets

METHODS AND APPARATUS FOR MOTION COMPENSATION IN IMAGE RECONSTRUCTION

CROSS REFERENCE TO RELATED APPLICATIONS

This application claims the benefits of U.S. Provisional Application No. 60/398,463, filed Jul. 25, 2002, and U.S. Provisional Application No. 60/397,658, filed Jul. 23, 2002, which are both hereby incorporated by reference in their entireties.

BACKGROUND OF THE INVENTION

This invention relates generally to computed tomographic (CT) imaging, Electron Beam computed tomography (EBT), and, more particularly, to methods and apparatus for facilitating a reduction in motion induced artifacts.

There continues to be a need for enhanced imaging. For example, U.S. Pat. No. 6,353,653 to Edic discloses a method using an interpolation algorithm to interpolate radiographs to more than one instant in time, and to reconstruct these radiographs to generate a 4-D image of the heart and coronary vasculature.

BRIEF DESCRIPTION OF THE INVENTION

In one aspect, a method for facilitating a reduction in motion artifacts is provided, the method includes comparing two sequential scanned images to determine motion.

In another aspect, a method for facilitating a reduction in motion artifacts is provided, wherein the method includes estimating a velocity of at least one pixel of a first image by comparing the first image with a second image, and correcting a sinogram using the estimated velocity.

In another aspect, a method for facilitating a reduction in motion artifacts is provided, wherein the method includes generating a velocity vector for each of a plurality of pixels of a first image, and calculating a deltaH(t) for each pixel where deltaH(t) is a time variation of intensity in CT numbers as caused by motion.

In yet another aspect, a computer is configured to compare two sequential scanned images to determine motion.

In still another aspect, an imaging system for facilitating a reduction in motion artifacts is provided. The system includes a gantry including a radiation source and a radiation detector, and a computer operationally coupled to the radiation source and the radiation detector. The computer is configured to receive information from the detector array, generate at least two sequential images from the received information, and compare the at least two sequential images to determine motion.

In one aspect, a computer readable medium encoded with a program is provided. The program is configured to estimate a velocity of at least one pixel of a first image by comparing the first image with a second image, and correct a sinogram using the estimated velocity.

In another aspect, an imaging system for facilitating a reduction in motion artifacts is provided. The system includes a gantry including a radiation source and a radiation detector, the radiation source including an electron beam source projecting an electron beam toward a target which emits x-rays toward the detector, and a computer operationally coupled to the radiation source and the radiation detector. The computer is configured to generate a velocity vector for a plurality of pixels of a first image, and calculate a deltaH(t) for each pixel where deltaH(t) is a time variation of intensity in CT numbers as caused by motion.

DETAILED DESCRIPTION OF THE INVENTION

Figure 1:
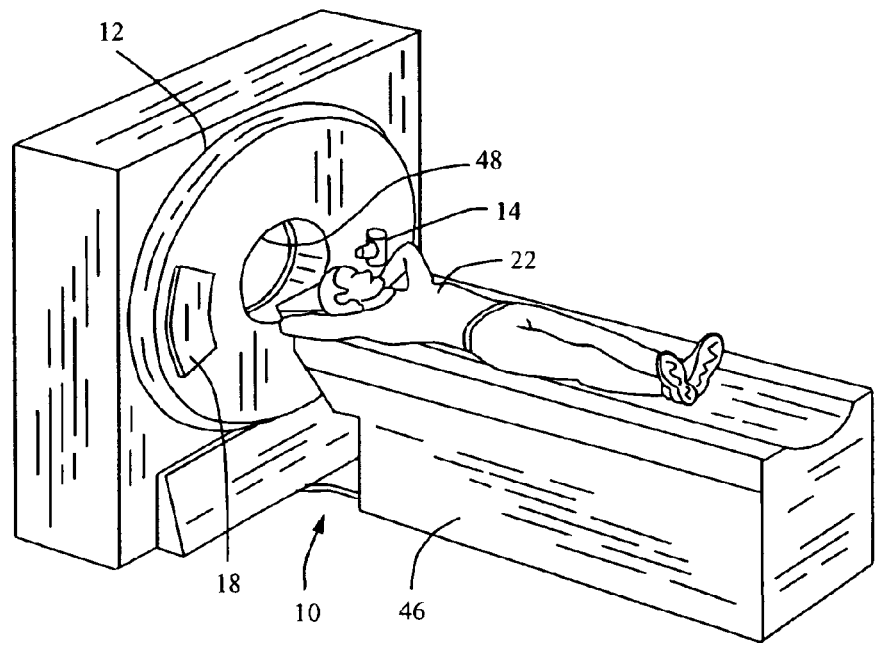
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector about the object or patient being imaged.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display or any other type of visual display.

To reduce the total scan time, a "helical" scan may be performed. To perform a "helical" scan, the patient is continually moved via the patient table while the projection data for the prescribed number of slices is acquired. The helix mapped out by the fan beam yields projection data from which images in each prescribed slice may be reconstructed.

Reconstruction algorithms for helical scanning typically use helical weighting algorithms that weight the collected data as a function of view angle and detector channel index. Specifically, prior to a filtered backprojection process, the data is weighted according to a helical weighting factor, which is a function of both the gantry angle and detector angle. The weighted data is then processed to generate CT numbers and to construct an image that corresponds to a two-dimensional slice taken through the object.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features. Moreover, the term "scanned image" can be either a CT image or an EBT image. Additionally, the methods disclosed herein apply equally well to volumetric CT scanners that employ area x-ray detectors, comprised of 2 or more detector rows.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
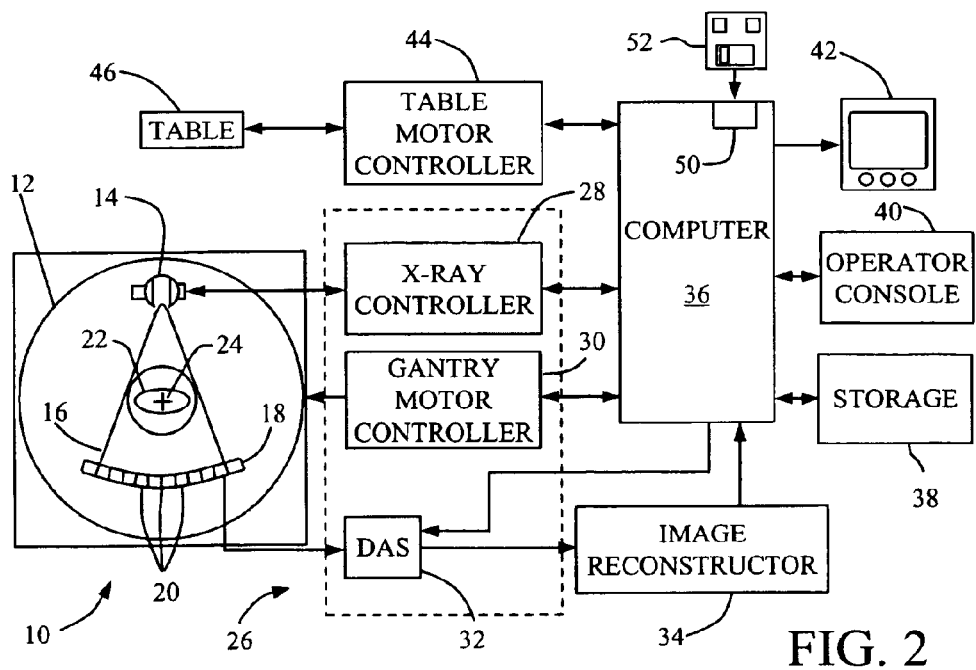
FIG. 2 is a block schematic diagram of the system illustrated in FIG. 1.

Referring to FIGS. 1 and 2, a multi-slice scanning imaging system, for example, a computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a patient 22. Each detector element 20 produces an electrical signal that represents the intensity of an impinging x-ray beam and hence allows estimation of the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is sent to a computer 36, which stores the image in a mass storage device 38.

Computer 36 also receives commands and scanning parameters from an operator via console 40 that has a keyboard. An associated visual display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 in gantry 12. In particular, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD, a MOD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Image reconstructor 34 may be specialized hardware or may be software executed within computer 36.

Figure 3:
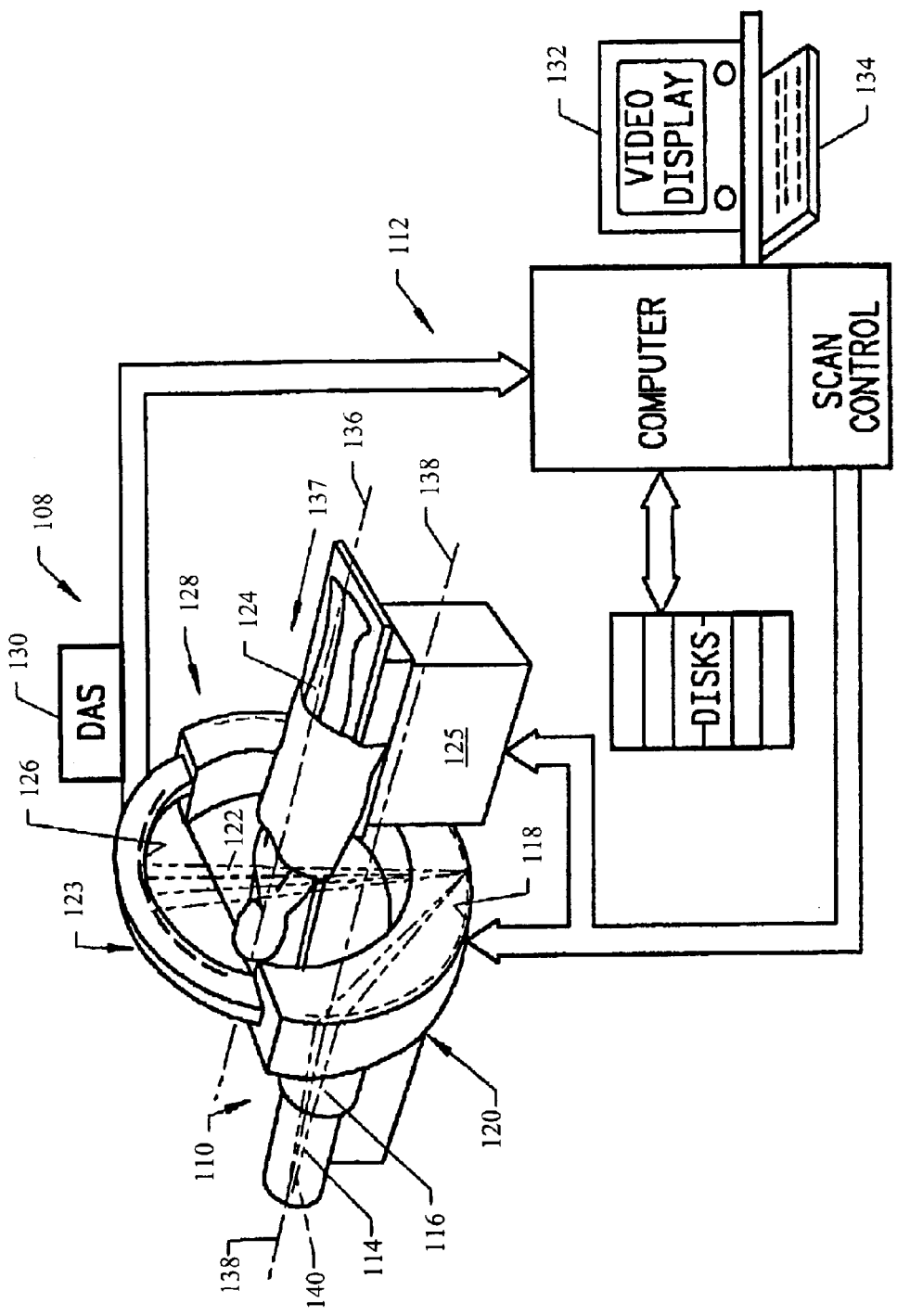
FIG. 3 depicts a computed tomography X-ray transmission scanning system utilizing electron beam technology.
Figure 4:
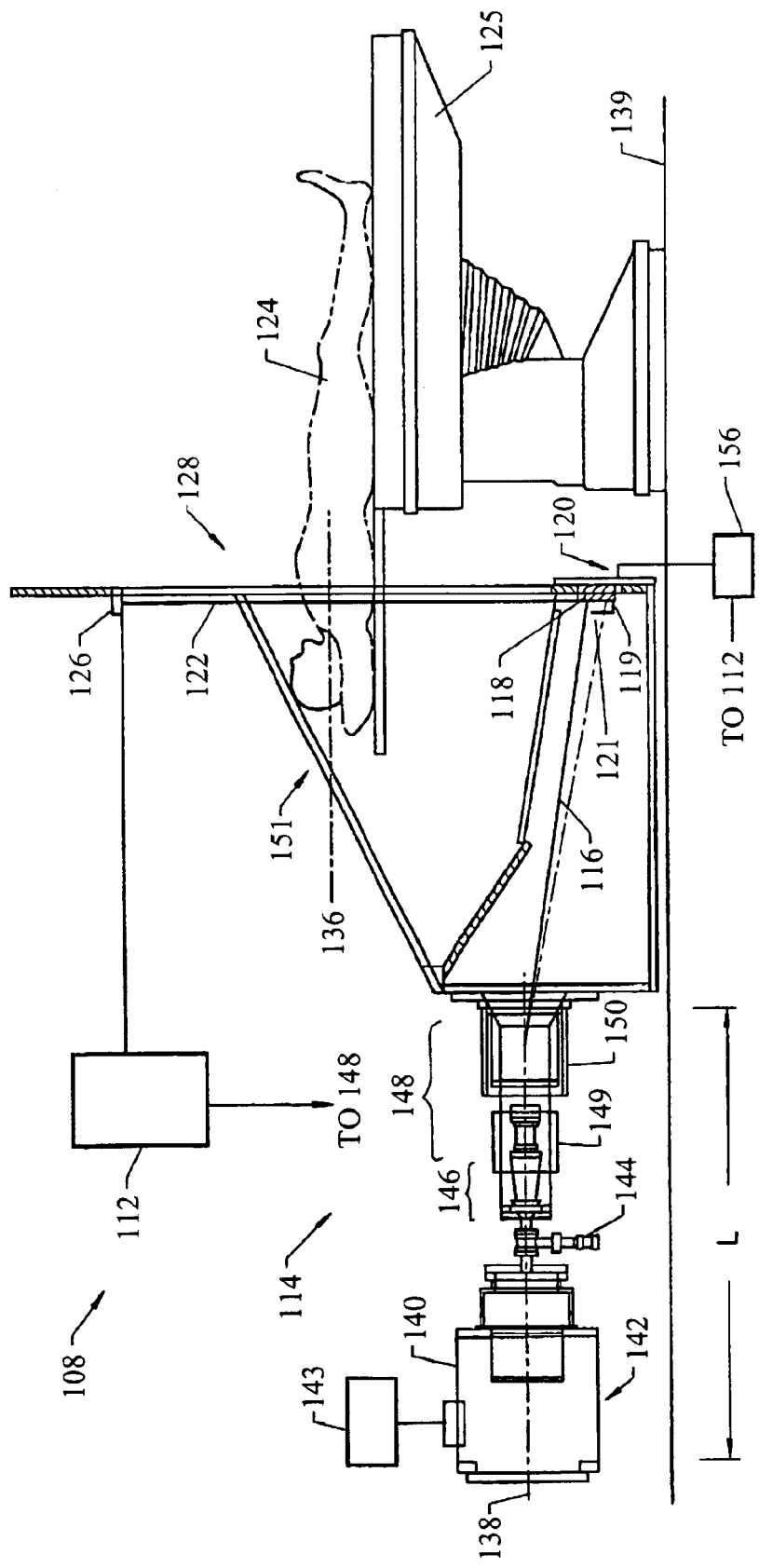
FIG. 4 depicts the system illustrated in FIG. 3.

FIGS. 3 and 4 depict a generalized off-axis computed tomography X-ray transmission scanning system 108 configured as herein described and also referred to as electron beam computed tomography system (EBT) 108. System 108 includes a scanner 110 and an associated computer system 112. Scanner 110 includes a vacuum housing chamber 114 wherein an electron beam 116 is generated and caused to scan an arc-shaped target 118 located within and extended around the inside of a front lower portion 120 of chamber 114. Typically, chamber 114 has a length of about 2 m, although other dimensions can also be used.

Upon being struck by the swept electron beam, which typically scans 210 degrees or so in about 50 ms, target 118 emits a moving fan-like beam of X-rays 122 that pass through a region of a subject 124 (e.g., a patient or other object) lying atop a couch moving mechanism 125, and then register upon a detector array 126 located diametrically opposite to target 118. The ring-like assembly housing target 118 and detector array 126 will be referred to collectively as a gantry 128. Target 118 and detector array 126 are concentric about a scanner axis 136, and define planes normal to that axis.

The detector array outputs data to a DAS 130 that digitizes and passes the data to computer system 112. Computer 112 further processes and records the data to produce a reconstructed image of a slice of subject 124 on a video monitor 132. An X-ray technician via a keyboard 134 operates computer system 112 to control the overall operation of system 108, including the production and control of electron beam 116 and movement of patient 124. It is understood that system 108 may be operated in a conventional mode and/or in a helical scanning mode.

The generation of the scanning electron beam 116 will now be described with reference to FIG. 4. An electron gun 140 within an upstream end 142 of chamber 114 produces electron beam 116 in response to high voltage excitation (e.g., 130 kV) from a power supply 143. Although a vacuum pump (not shown) evacuates chamber 114, gases remain that can produce positive ions in the presence of the electron beam 116.

An electrode assembly 146 is disposed within the chamber 114 coaxially along an optic or beam system axis 138, such that electron beam 116 passes axially therethrough. Electrode assembly 146 is part of the optical system.

Electrode assembly 146 clears ions from beam 116 that are produced when beam 116 interacts with the residual nitrogen gas in vacuum chamber 114. This reduces the ion bombardment of the cathode and allows beam 116 to expand under the influence of its self-electric field. Beyond the electrode assembly ions accumulate in the beam until the beam is neutralized, in this neutralized region, beam 116 is plasma focused under the influence of its self-magnetic field. A plurality of magnets 148 including a solenoid magnet 149 and a dipole and a quadrupole magnet 150 are used to adjust the focusing of beam 116 and to deflect beam 116 to target 118. Also, solenoid magnet 149 surrounds part of electrode assembly 146.

Although the following description is in the context of an EBT scanner with a 33–50 msec acquisition time, the herein described methods are applicable to any kind of scanner that measures projection data at a frequency that is fast enough so that object motion present is sampled frequently enough to capture pertinent information, as known in the literature as sampling greater than or equal to the Nyquist sampling rate.

In CT and EBT scanners 10 and 108, scan data can be accumulated continuously at each of several levels. In one embodiment, for EBT scanner 108, the time for a scan is either 33 or 50 milliseconds. Each projection during the scan has a time resolution of 0.02 milliseconds, and projections are measured linearly over a range of 212 degrees, for example, starting from time zero and ending at time 33 or 50 milliseconds. Although the individual projections have good time resolution, the fact that the entire sinogram is spread over time introduces motion artifacts and blurring when an image is reconstructed. Each fast projection in the sinogram is sampled approximately every 50 milliseconds in a continuous scan sequence. The herein described methods and apparatus time interpolate at least one sinogram to remove the time skewing, resulting in sharper CT image than previously obtained. Therefore, one technical effect of the herein described apparatus and methods is an increased sharpness in reconstructed CT images.

The goal is to correct a data sinogram that is obtained over a range of times to a new time-interpolated sinogram equivalent to what would have been obtained if the projection data had been gathered simultaneously. In one embodiment, two sequential 33–50 msec EBT images are compared with an edge recognition program. A velocity image is developed that shows the velocity vector for each pixel in the average image based on comparison of edge motions between the two original images. The velocity image is then used to compute a time-interpolated sinogram at a specific intermediate time or times, with a time resolution of less than 10 msec. The interpolated sinogram is then reconstructed into an image with less motion artifact.

If object motion in the original reconstructions (33 msec or 50 msec reconstructions) is sufficient to cause image artifacts, the best motion estimates for pixels in these images are determined. As described above, the motion estimates are used to generate new reconstructions with improved temporal resolution and reduced artifacts. The set of new reconstructions can be used to refine the motion of pixels in the image in a similar fashion, resulting in an iterative approach to incrementally improve the temporal resolution in reconstructions.

Each pixel in a CT image corresponds to a unique curve in the original CT scan acquisition data. Since these curves resemble sinusoidal functions, the data matrix is called a sinogram. If the point is moving during sinogram acquisition, the sinusoidal curve will be distorted reflecting the influence of the motion. Therefore, if the velocity of a pixel in the image is estimated, through comparison of two images at nearby times, then a correction can be calculated for the sinogram, such that the corrected sinogram reflects data at constant time. Since CT reconstruction is a linear process, a method is developed for a single pixel representing a single point object, and the method is extended to the entire image and used to correct a complete sinogram of acquisition data. The time-corrected sinogram is then reconstructed, resulting in a motion-free CT image or an image with reduced motion artifacts. Additionally, this method does not require the motion to be periodic, rather, any kind of motion can be corrected, providing the sampling scans are fast enough. In other words, the method can be done during a single cycle if the motion is periodic. Additionally, motion artifacts can be reduced for non-periodic motion as well using the herein described methods and apparatus. This reduction in motion artifacts is one technical effect of the herein described methods and apparatus.

An iterative approach, implemented by repeating the process described above, can be used to further improve the temporal resolution of reconstructed images. For example, given N sinograms, labeled 1' to N', N images are generated 1* to N*, 1* is compared to 2* and a corrected sinogram (1") is generated, 2* is compared to 3* and another corrected sinogram (2") is generated, and so forth. Corrected images 1 and 2 are then generated from corrected sinograms 1" and 2" respectively, 1 is compared to 2 and a new corrected sinogram (1''') is generated, and so forth.

In one embodiment, a warped image grid is used in reconstruction of the image. The temporal resolution of the image of the moving object, such as a heart, is improved, and a 3-D reconstruction of the image of the heart at various phases of the motion is provided. In this aspect, the motion of the moving object, such as a heart, is estimated, and this estimation is used to construct a warped image grid as a function of the movement of the moving object. The warped image grid is indicative of the position of the moving object at a particular part of the motion of the moving object during the data acquisition process. Once the warped image grid as a function of time during the data acquisition process is constructed and an image with reduced motion artifacts reconstructed, the motion estimation that allowed generation of the warped grid may be used along with knowledge of its position at that part of the motion to reconstruct an image of the object at any other part of a motion. The process is repeated for each parts of the motion of interest to provide a 4-D reconstruction of the moving object, such as a heart as is described in U.S. Provisional Application No. 60/397,658, and U.S. patent application Ser. No. 10/625,361 filed Jul. 23, 2003 which claims the benefit of U.S. Provisional Application No. 60/397,658, and which is also incorporated by reference in its entirety.

In other words, a scan is performed conventionally wherein projection data acquired will have inconsistencies arising because of cardiac motion. For example, the projection data for a particular view will depend upon the particular motion of the heart when the data was acquired. The warped image grid accounts for the position of the heart during a particular motion. From the set of 3D volumetric images, the warping of the reconstruction image grid to account for the inconsistencies in the projection data are then determined for each set of adjacent 3D volumetric images, by estimating how the objects in the images are moving within the sequence of 3D volumetric images. The motion estimates allowing generation of the warped image grid as a function of time or view angle position during the data acquisition process are used during the reconstruction process to reduce motion artifacts.

Another way to determine the warped image grid is to use the projection data and the fact that the projection data vary slowly from view position to view position. The warping of the image space to account for the inconsistencies identified in the 2D projection data and a warped image grid is determined for each slice of interest.

In another embodiment, velocity vectors from motion estimation are used to calculate deltaH(t) for each pixel, where deltaH(t) refers to the time variation of intensity in Hounsfield numbers (CT numbers) of the pixels as caused by motion. The motion estimation can be from the above described methods to generate a warped image grid, from the above described velocity image, and any other motion estimation that includes velocity vectors on a pixel by pixel basis or from which pixel wise velocity vectors are derivable. In one embodiment, the deltaH(t)s are forward projected to produce projection corrections for each line in the sinogram as a function of time. The corrected sinogram is then reconstructed. Alternatively, one can forward project the deltaH(t)s into a delta sinogram, and then reconstruct the delta sinogram as a correction to be added to the picture. This is different from calculating intermediate pictures by interpolation because the intermediate pictures with the motion estimation scheme are based on velocity, not linear intensity averages. This puts moving edges where they belong. And it is also different from the sinogram interpolation of intensities, although, in one embodiment, the motion estimation is applied directly to the sinograms, rather than the images.

In another embodiment, the motion estimation based on the images is used to correct the sinograms, wherein the motion is estimated using the kind of motion predictor used in MPEG encoding, or by spatially warping one image to fit the other using the techniques developed for image morphing software. Although the description is based on an EBT scanner with a 33–50 msec-acquisition time, the method is applicable to any kind of scanner that measures projection data at a frequency that is fast enough so that object motion present is sampled frequently enough such that motion betweens samples is appropriately captured, as known in the literature as sampling greater than or equal to the Nyquist sampling rate.

For example, in CT, EBT, and MRI scanners, scan data can be accumulated continuously at each of several levels. As stated above, and for the newest EBT scanners, the time for a scan is either 33 or 50 milliseconds. Each projection during the scan has a time resolution of 0.02 milliseconds, and projections are measured sequentially over a range of 212 degrees, for example, starting from time zero and ending at time 33 or 50 milliseconds. Although the individual projections have excellent time resolution, the data set is skewed over the time interval of either 33 or 50 milliseconds. This skewing introduces motion artifacts and blurring when the image is reconstructed. If two or more scans are performed in sequence then it is possible to compare two sequential images in order to determine a measure of the amount of motion that is occurring during the scan interval. A number of algorithms for characterizing motion in a sequence of images have been developed for other applications. MPEG encoding is used extensively in the video industry and uses motion prediction from frame to frame to compress video data over time. Image morphing software is used to compare two images and estimate a set of intermediate images, which represent the motion required to blend one image into another. The motion prediction can be found for each pixel in the image using the above methods and used to estimate a function over time that describes the change in intensity value for each pixel at intermediate times between the two frames that are compared. Thus, a set of intermediate pictures is computed similar to the processes used in image morphing. The intermediate pictures are then forward projected at the appropriate angles to produce corrected projections in the scan data at the corresponding angle and time. In an exemplary embodiment, the motion estimate is used to compute a set of image correction values vs. time, and these small delta corrections are forward projected to yield a correction raw data set. The projection corrections are then reconstructed into a correction image applied to the original frame. Since only small corrections are involved it is possible to perform a second step iteration to produce an even more accurate motion-compensated reconstruction.

In an alternative embodiment, a pair of sequential data sets is compared. The data is generally arranged as a two-dimensional data array such that projections are in sequential rows. This arrangement is referred to as a sinogram, since an individual object point traces a sinusoidal curve in the representation. In one form of a sinogram representation known as a convolved sinogram, edges can be seen that correspond to edge features in the scanned object. The motion of such an edge as seen by comparing the sequential sinograms is measured and used to estimate the motion for the entire sinogram as a function of time, for each individual projection ray. Using these values, a new corrected sinogram at constant time is computed, and the corrected sinogram reconstructed to produce a motion corrected image.

While the invention has been described in terms of various specific embodiments, those skilled in the art will recognize that the invention can be practiced with modification within the spirit and scope of the claims.

What is claimed is:

1. A method for facilitating a reduction in motion artifacts, said method comprising comparing two sequential scanned images with an edge recognition program to determine motion.

2. A method in accordance with claim 1 further comprising developing a velocity image which shows a velocity vector for each pixel in an average image based on comparison of edge motions between the two original images.

3. A method in accordance with claim 2 further comprising using the velocity image to compute a time-interpolated sinogram at a specific intermediate time.

4. A method in accordance with claim 3 further comprising reconstructing an image using the interpolated sinogram.

5. A method in accordance with claim 1, wherein said comparing further comprises comparing two sequential images to generate a warped image grid.

6. A method in accordance with claim 1, wherein said comparing further comprises comparing two sequential images to determine a plurality of velocity vectors.

7. A method in accordance with claim 6 further comprising using the velocity vectors to calculate a deltaH(t) for each pixel where deltaH(t) is a time variation of intensity in CT numbers as caused by motion.

8. A method for facilitating a reduction in motion artifacts, said method comprising comparing two sequential scanned images to determine motion using an mpeg motion predictor.

9. A method for facilitating a reduction in motion artifacts, said method comprising comparing two sequential scanned images to determine motion and to generate an intermediate image representative of motion required to blend one said sequential image into the other said sequential image.

10. A method in accordance with claim 9 further comprising forward projecting the intermediate image to produce a corrected projection.

11. A method in accordance with claim 9 further comprising:
generating a set of image correction values referenced by time using the intermediate image;
forward projecting the generated set to produce a correction raw data set;
reconstructing a correction image using the correction raw data set; and
adding the correction image to an image to be corrected to produce a first corrected image.

12. A method in accordance with claim 11 further comprising:
producing a second corrected image;
comparing the first and second corrected images to generate an intermediate corrected image representative of motion required to blend the first corrected image into the second corrected image; and
using the intermediate corrected image to further correct the first corrected image.

13. A method for facilitating a reduction in motion artifacts, said method comprising:
estimating a velocity of at least one pixel of a first image by comparing the first image with a second image; and
correcting a sinogram using the estimated velocity.

14. A method in accordance with claim 13 further comprising:
generating a first corrected image using the corrected sinogram;
estimating a velocity of at least one pixel of the first corrected image by comparing the first corrected image with a third image comprising a corrected image;
correcting a sinogram using the estimated velocity of the at least one pixel of the first corrected image.

15. A method for facilitating a reduction in motion artifacts, said method comprising:
generating a velocity vector for each of a plurality of pixels of a first image; and
calculating a deltaH(t) for each pixel where deltaH(t) is a time variation of intensity in CT numbers as caused by motion.

16. A method in accordance with claim 15 further comprising:
forward projecting the deltaH(t)s to produce projection corrections for each line of a sinogram as a function of time; and
reconstructing a second image using the corrected sinogram.

17. A method in accordance with claim 15 further comprising:
forward projecting the deltaH(t)s to generate a deltaH(t) sinogram;
reconstructing a second image using the deltaH(t) sinogram; and
adding the second image to the first image to generate a corrected image.

18. A computer configured to compare two sequential scanned images with an edge recognition program to determine motion and generate a warped image grid.

19. A computer in accordance with claim 18 further configured to develop a velocity image, which shows a velocity vector for each pixel in an average image, based on comparison of edge motions between the two original sequential scanned images.

20. A computer in accordance with claim 19 further configured to use the velocity image to compute a time-interpolated sinogram at a specific intermediate time.

21. A computer in accordance with claim 20 further configured to reconstruct an image using the interpolated sinogram.

22. A computer in accordance with claim 18 further configured to compare two sequential images to determine a plurality of velocity vectors.

23. A computer in accordance with claim 22 further configured to use the velocity vectors to calculate a deltaH(t) for each pixel where deltaH(t) is a time variation of intensity in CT numbers as caused by motion.

24. A computer configured to compare two sequential scanned images to determine motion, generate a warped image grid, and to generate an intermediate image representative of motion required to blend one said sequential scanned image into the other said sequential scanned image.

25. A computer in accordance with claim 24 further configured to forward project the intermediate image to produce a corrected projection.

26. A computer configured to compare two sequential scanned images to determine motion and generate a warped image grid and further configured to:
generate a set of image correction values referenced by time using an intermediate image;
forward project the generated set of image correction values to produce a correction raw data set;
reconstruct a correction image using the correction raw data set; and
add the correction image to an image to be corrected to produce a first corrected image.

27. A computer in accordance with claim 26 further configured to:
produce a second corrected image;
compare the first and second corrected images to generate an intermediate corrected image representative of motion required to blend the first corrected image into the second corrected image; and
use the intermediate corrected image to further correct the first correct image.

28. An imaging system for facilitating a reduction in motion artifacts comprising:
a gantry comprising a radiation source and a radiation detector; and
a computer operationally coupled to said radiation source and said radiation detector, said computer configured to:
receive information from said detector array;
generate at least two sequential images from the received information; and
compare said at least two sequential images with an edge detection program to determine motion and generate a warped image grid.

29. An imaging system in accordance with claim 28, wherein said radiation source comprises an electron beam source projecting an electron beam toward a target which emits x-rays toward said detector.

30. An imaging system in accordance with claim 28, wherein said computer further configured to compare the two sequential images with an edge recognition program.

31. An imaging system in accordance with claim 30, said computer further configured to develop a velocity image which shows a velocity vector for each pixel in an average image based on comparison of edge motions between the two original sequential scanned images.

32. A computer readable medium encoded with a program configured to:
estimate a velocity of at least one pixel of a first image by comparing the first image with a second image; and correct a sinogram using the estimated velocity.

33. A medium in accordance with claim 32 wherein said program further configured to:

generate a first corrected image using the corrected sinogram;

estimate a velocity of at least one pixel of the first corrected image by comparing the first corrected image with a third image comprising a corrected image;

correct a sinogram using the estimated velocity of the at least one pixel of the first corrected image.

34. An imaging system for facilitating a reduction in motion artifacts, said system comprising:

a gantry comprising a radiation source and a radiation detector, said radiation source comprising an electron beam source projecting an electron beam toward a target which emits x-rays toward said detector; and a computer operationally coupled to said radiation source and said radiation detector, said computer configured to:

generate a velocity vector for a plurality of pixels of a first image; and calculate a deltaH(t) for each pixel where deltaH(t) is a time variation of intensity in CT numbers as caused by motion.

35. A system in accordance with claim 34 wherein said computer further configured to:

forward project the deltaH(t)s to produce projection corrections for each line of a sinogram as function of time; and reconstruct a second image using the corrected sinogram.

* * * * *

UNITED STATES PATENT AND TRADEMARK OFFICE
CERTIFICATE OF CORRECTION

PATENT NO. : 6,934,357 B2
APPLICATION NO. : 10/625719
DATED : August 23, 2005
INVENTOR(S) : Boyd et al.

It is certified that error appears in the above-identified patent and that said Letters Patent is hereby corrected as shown below:

In Claim 35, column 12, line 12, between "as" and "function" insert -- a --.

Signed and Sealed this

Twentieth Day of November, 2007

JON W. DUDAS
*Director of the United States Patent and Trademark Office*